United States Patent
Im et al.

(10) Patent No.: US 11,045,498 B2
(45) Date of Patent: Jun. 29, 2021

(54) NONVIRAL MINICIRCLE VECTOR CARRYING SOX GENE AND CONSTRUCTION METHOD THEREFOR

(71) Applicant: DONGGUK UNIVERSITY INDUSTRY-ACADEMIC COOPERATION FOUNDATION, Seoul (KR)

(72) Inventors: Gun Il Im, Anyang-si (KR); Jong Min Lee, Goyang-si (KR); Ji Yun Ko, Goyang-si (KR)

(73) Assignee: DONGGUK UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 315 days.

(21) Appl. No.: 16/097,698

(22) PCT Filed: Jun. 16, 2017

(86) PCT No.: PCT/KR2017/006328
§ 371 (c)(1),
(2) Date: Oct. 30, 2018

(87) PCT Pub. No.: WO2018/030630
PCT Pub. Date: Feb. 15, 2018

(65) Prior Publication Data
US 2019/0224241 A1    Jul. 25, 2019

(30) Foreign Application Priority Data

Aug. 10, 2016 (KR) .......................... 10-2016-0101761

(51) Int. Cl.
| | |
|---|---|
| *A61K 35/28* | (2015.01) |
| *C07K 14/47* | (2006.01) |
| *C12N 15/85* | (2006.01) |
| *A61K 48/00* | (2006.01) |
| *A61K 35/00* | (2006.01) |
| *A61K 38/00* | (2006.01) |
| *C12N 15/90* | (2006.01) |

(52) U.S. Cl.
CPC .......... *A61K 35/28* (2013.01); *A61K 48/0066* (2013.01); *C07K 14/47* (2013.01); *C12N 15/85* (2013.01); *A61K 35/00* (2013.01); *A61K 38/00* (2013.01); *C12N 15/907* (2013.01); *C12N 2840/20* (2013.01); *C12Y 301/22001* (2013.01); *Y02A 50/30* (2018.01)

(58) Field of Classification Search
CPC .................................................... A61K 35/28
See application file for complete search history.

(56) References Cited

U.S. PATENT DOCUMENTS

2014/0289882 A1    9/2014   Zhu et al.
2016/0220699 A1    8/2016   O'Heeron

OTHER PUBLICATIONS

Narsinh et al. (Nature Protocols, (2011; published online on Dec. 23, 2010); 6(1): 78-88). (Year: 2011).*
Kim et al. (56th Annual Meeting of the Orthopaedic Research Society, Poster No. 780 (Mar. 2010) (Year: 2010).*
International Search Report of the International Searching Authority corresponding to International Patent Application No. PCT/KR2017/006328, dated Sep. 12, 2017. (3 pages).
Park et al. "Chondrogenesis of human mesenchymal stem cells mediated by the combination of SOX trio SOX5, 6, and 9 genes complexed with PEI-modified PLGA nanoparticles" Biomaterials 32:3679-3688 (2011).
Im et al. "Chondrogenesis of adipose stem cells in a porous PLGA scaffold impregnated with plasmid DNA containing SOX trio (SOX-5, -6, and -9) genes" Biomaterials 32:4385-4392 (2011).
Kim et al. "Nonviral transfer of Sox-trio gene to adipose stem cells using a microporator" 56th Annual Meeting of the Orthopaedic Research Society, Poster No. 780. (Mar. 2010).
Narsinn et al. "Generation of adult human induced pluripotent stem cells using nonviral minicircle DNA vectors" Nature Protocols 6(1):78-88 (2011).

* cited by examiner

*Primary Examiner* — Scott Long
(74) *Attorney, Agent, or Firm* — Myers Bigel, P.A

(57) ABSTRACT

The present invention relates to a non-viral minicircle vector expressing a SOX gene, a stem cell into which the vector is introduced, a pharmaceutical composition for preventing or treating a cartilage disease, including the stem cell, and a method for constructing the vector. The transformation of mesenchymal stem cells with MC/SOX-Trio or MC/SOX-Duo, which is a non-viral minicircle vector according to the present invention, can completely exclude the necessity of expensive growth factors that have been indispensably used in inducing the differentiation of mesenchymal stem cells into chondrocytes. Accordingly, the mesenchymal stem cells transformed therewith, when implanted in vivo, can differentiate into chondrocytes by themselves, and thus have an advantage capable of simplifying the existing complicated steps of culturing cells to induce differentiation and then transplanting the cells.
Further, unlike existing vector systems in which antibiotic-resistant genes and other bacteria-derived exogenous genes are simultaneously transferred to cells even after transformation, the vector of the present invention minimizes transfer of unnecessary genes into target cells by allowing two or three SOX genes necessary only for differentiation into chondrocytes to be regulated under one promoter, and thus can be utilized as a non-viral vector system in the most advantageous form for use in clinical application of stem cell-gene therapeutic agents.

15 Claims, 6 Drawing Sheets

Specification includes a Sequence Listing.

[FIGURE 1]
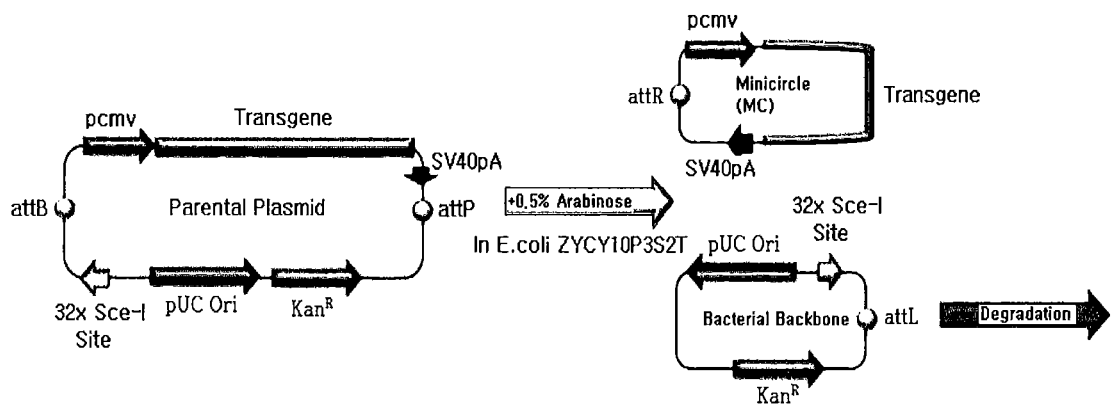
[FIGURE 2]
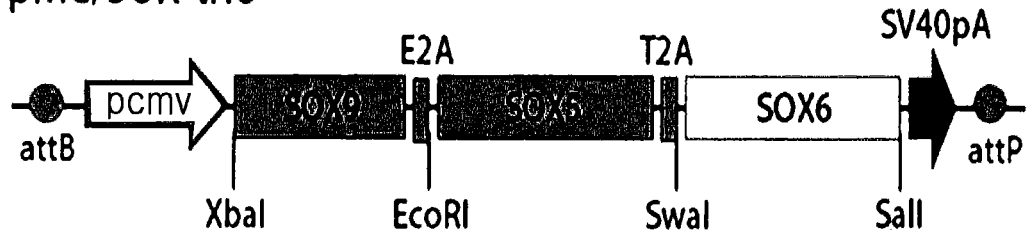
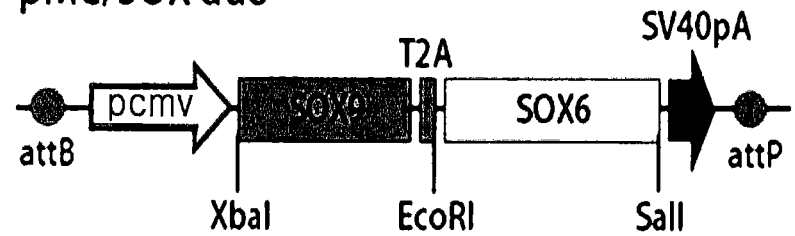

[FIGURE 3]
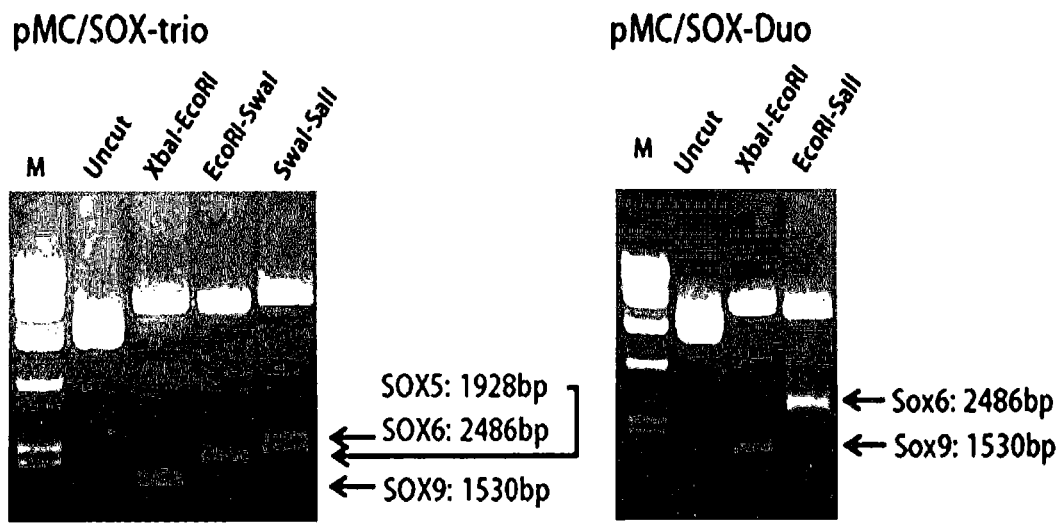
[FIGURE 4]
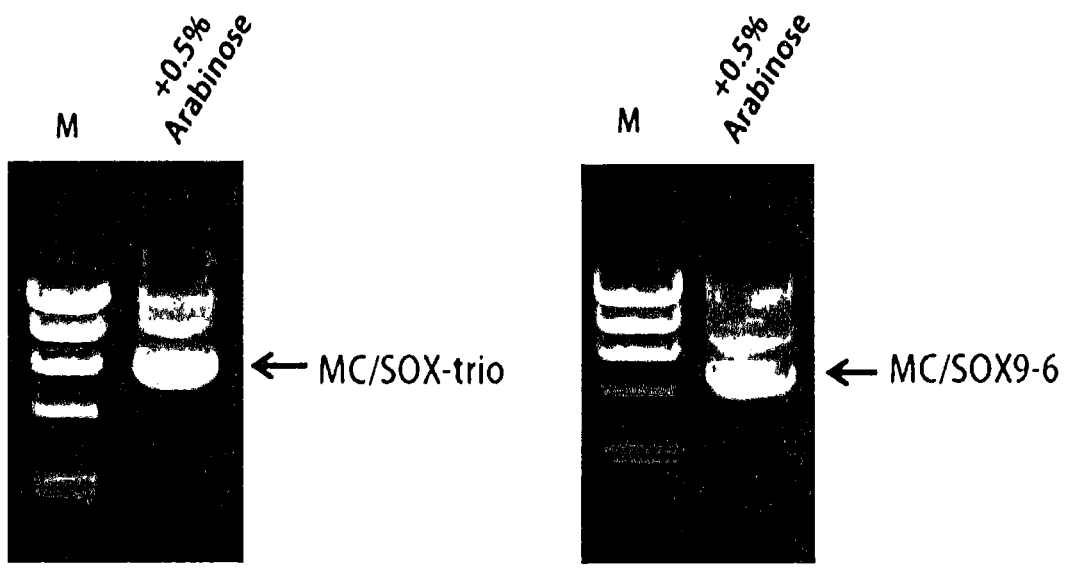

[Figure 5]
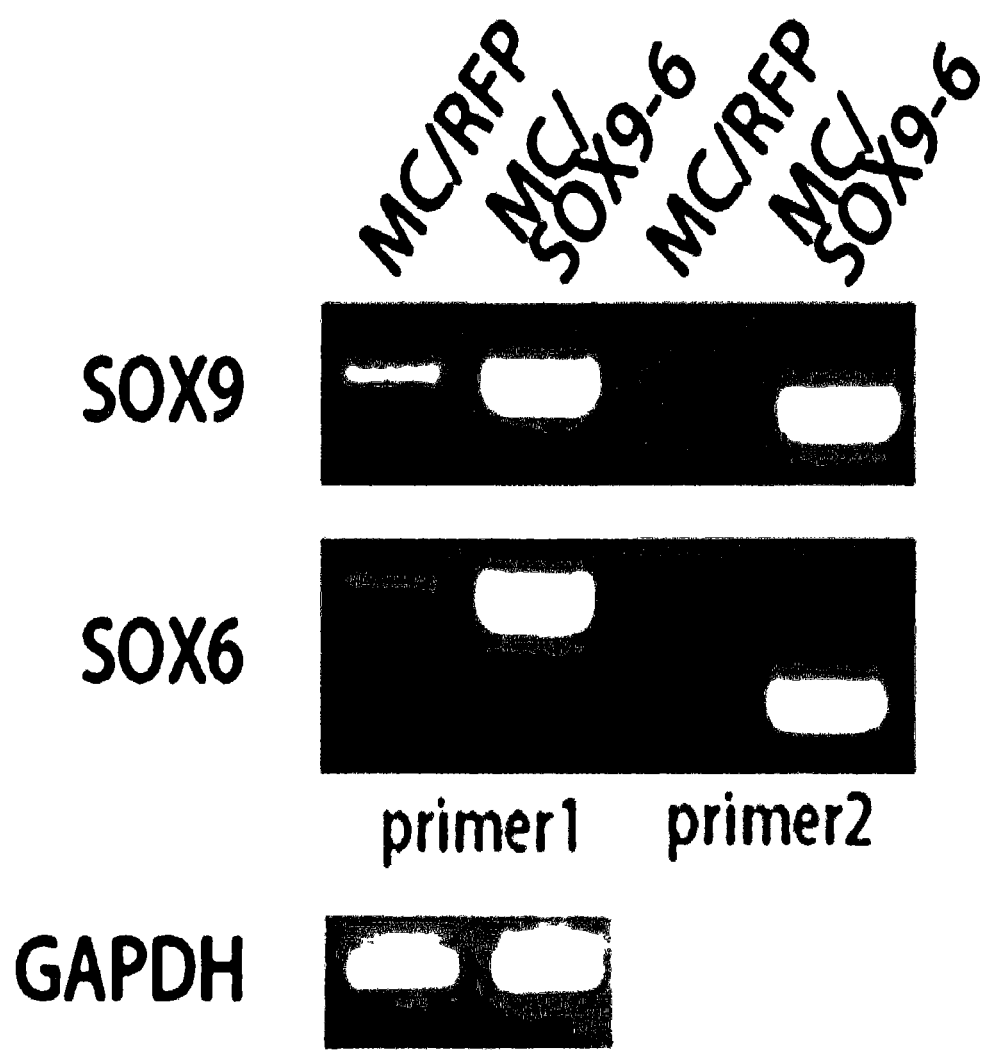

[Figure 6]
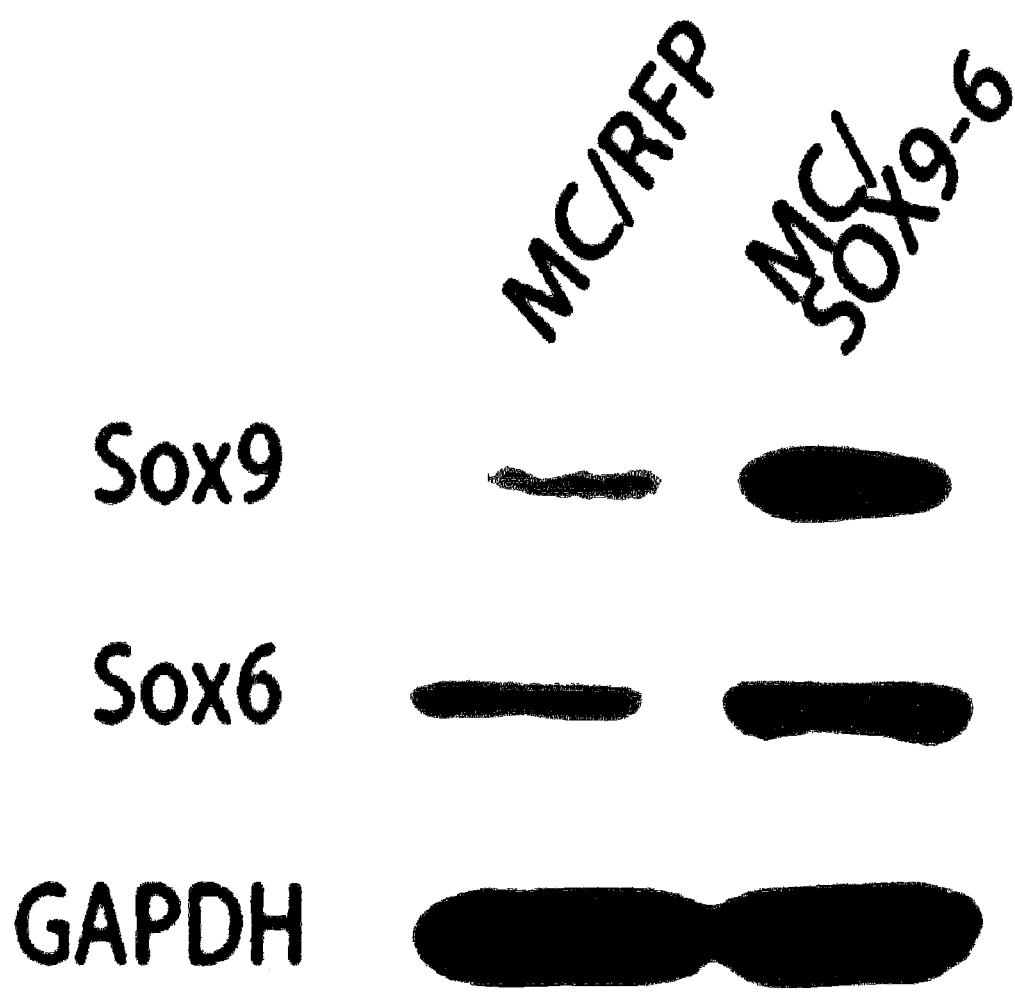

[Figure 7]
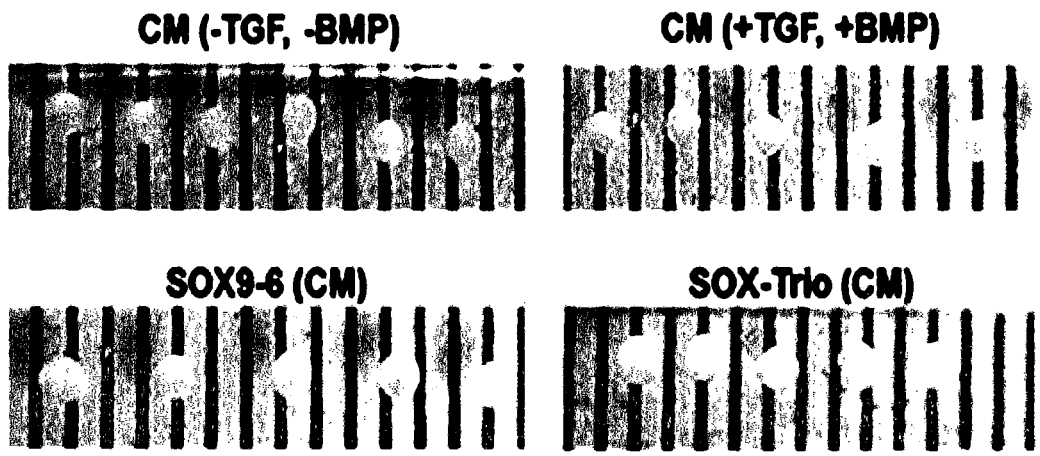
[Figure 8]
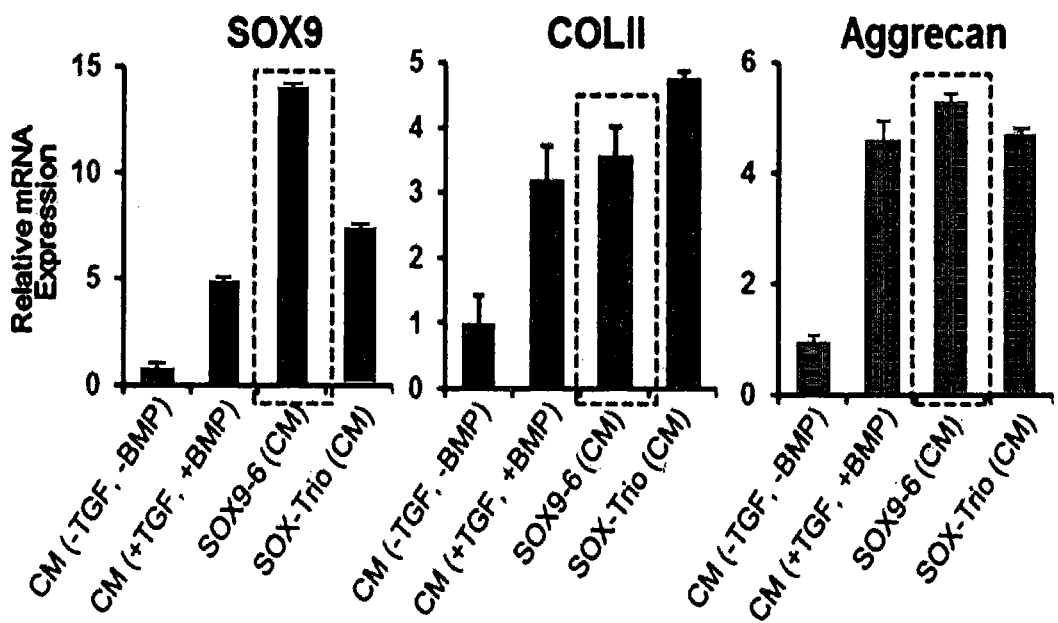

[Figure 9]
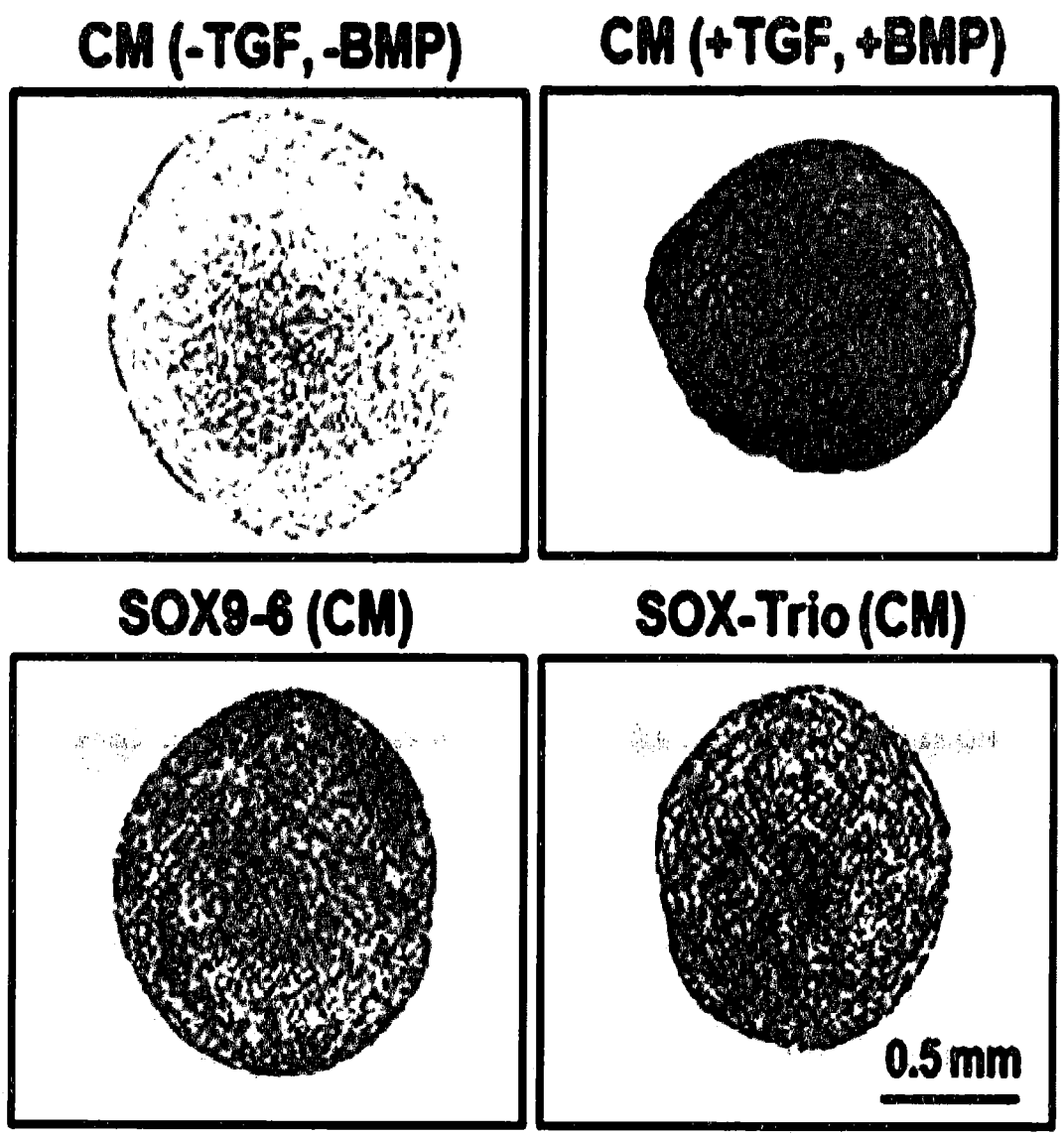

SEQUENCE LISTING

<160> NUMBER OF SEQ ID NOS: 12

<210> SEQ ID NO 1
<211> LENGTH: 7846
<212> TYPE: DNA
<213> ORGANISM: Artificial
<220> FEATURE:
<223> OTHER INFORMATION: MC/SOX-Trio

<400> SEQUENCE: 1

| | | | | |
|---|---|---|---|---|
| tgccagggcg | tgcccttggg | ctccccgggc | gcgactagtg | aattgatact | agtattatgc | 60 |
| ccagtacatg | accttatggg | actttcctac | ttggcagtac | atctacgtat | tagtcatcgc | 120 |
| tattaccatg | gtgatgcggt | tttggcagta | catcaatggg | cgtggatagc | ggtttgactc | 180 |
| acggggattt | ccaagtctcc | accccattga | cgtcaatggg | agtttgtttt | ggcaccaaaa | 240 |
| tcaacgggac | tttccaaaat | gtcgtaacaa | ctccgcccca | ttgacgcaaa | tgggcggtag | 300 |
| gcgtgtacgg | tgggaggttt | atataagcag | agctcgttta | gtgaaccgtc | agatcgcctg | 360 |
| gagacgccat | ccacgctgtt | ttgacctcca | tagaagattc | tagatctaga | gccaccatga | 420 |
| atctcctgga | cccttcatg | aagatgaccg | acgagcagga | aagggcctg | tccggcgccc | 480 |
| ccagccccac | catgtccgag | gactccgcgg | gctcgccctg | cccgtcgggc | tccggctcgg | 540 |
| acaccgagaa | cacgcggccc | caggagaaca | cgttccccaa | gggcgagccc | gatctgaaga | 600 |
| aggagagcga | ggaggacaag | ttccccgtgt | gcatccgcga | ggcggtcagc | caggtgctca | 660 |
| aaggctacga | ctggacgctg | gtgcccatgc | cggtgcgcgt | caacggctcc | agcaagaaca | 720 |
| agccgcacgt | caagcggccc | atgaacgcct | tcatggtgtg | ggcgcaggcg | cgcgcagga | 780 |
| agctcgcgga | ccagtacccg | cacttgcaca | acgccgagct | cagcaagacg | ctgggcaagc | 840 |
| tctggagact | tctgaacgag | agcgagaagc | ggcccttcgt | ggaggaggcg | gagcggctgc | 900 |
| gcgtgcagca | caagaaggac | cacccggatt | acaagtacca | gccgcggcgg | aggaagtcgg | 960 |
| tgaagaacgg | gcaggcggag | cagaggagg | ccacggagca | gacgcacatc | tcccccaacg | 1020 |
| ccatcttcaa | ggcgctgcag | gccgactcgc | cacactcctc | ctccggcatg | agcgaggtgc | 1080 |
| actccccgg | cgagcactcg | gggcaatccc | agggcccacc | gaccccaccc | accaccccca | 1140 |
| aaaccgacgt | gcagccgggc | aaggctgacc | tgaagcgaga | ggggcgcccc | ttgccagagg | 1200 |
| ggggcagaca | gccccctatc | gacttccgcg | acgtggacat | cggcgagctg | agcagcgacg | 1260 |
| tcatctccaa | catcgagacc | ttcgatgtca | acgagtttga | ccagtacctg | ccgcccaacg | 1320 |
| gccacccggg | ggtgccggcc | acgcacggcc | aggtcaccta | cacgggcagc | tacggcatca | 1380 |
| gcagcaccgc | ggccacccg | gcgagcgcgg | gccacgtgtg | gatgtccaag | cagcaggcgc | 1440 |
| cgccgccacc | cccgcagcag | cccccacagg | ccccgccggc | cccgcaggcg | ccccgcagc | 1500 |
| cgcaggcggc | gccccacag | cagccggcgg | caccccgca | gcagcacag | gcgcacacgc | 1560 |
| tgaccacgct | gagcagcgag | ccgggccagt | cccagcgaac | gcacatcaag | acggagcagc | 1620 |
| tgagccccag | ccactacagc | gagcagcagc | agcactcgcc | caacagatc | gcctacagcc | 1680 |
| ccttcaacct | cccacactac | agccctcct | acccgcccat | cacccgctca | cagtacgact | 1740 |
| acaccgacca | ccagaactcc | agctcctact | acagccacgc | ggcaggccag | ggcaccggcc | 1800 |
| tctactccac | cttcacctac | atgaacccg | ctcagcgccc | catgtacacc | cccatcgccg | 1860 |
| acacctctgg | ggtcccttcc | atccgcagga | cccacagccc | ccagcactgg | gaacaaccg | 1920 |
| tctacacaca | gctcactcga | cctatgcatt | caaacgggtc | gggtcaatgt | actaactacg | 1980 |
| ctttgttgaa | actcgctggc | gatgttgaaa | gtaataaccc | cggtcctgaa | ttcatgtctt | 2040 |

```
ccaagcgacc agcctctccg tatggggaag cagatggaga ggtagccatg gtgacaagca    2100
gacagaaagt ggaagaagag gagagtgacg ggctcccagc ctttcacctt cccttgcatg    2160
tgagttttcc caacaagcct cactctgagg aatttcagcc agtttctctg ctgacgcaag    2220
agacttgtgg ccataggact cccacttctc agcacaatac aatggaagtt gatggcaata    2280
aagttatgtc ttcatttgcc ccacacaact catctacctc acctcagaag gcagaagaag    2340
gtgggcgaca gagtggcgag tccttgtcta gtacagccct gggaactcct gaacggcgca    2400
agggcagttt agctgatgtt gttgacacct tgaagcagag gaaaatggaa gagctcatca    2460
aaaacgagcc ggaagaaacc cccagtattg aaaaactact ctcaaaggac tggaaagaca    2520
agcttcttgc aatgggatcg gggaactttg gcgaaataaa agggactccc gagagcttag    2580
ctgagaaaga aaggcaactc atgggtatga tcaaccagct gaccagcctc cgagagcagc    2640
tgttggctgc ccacgatgag cagaagaaac tagctgcctc tcagattgag aaacagcgtc    2700
agcaaatgga gctggccaag cagcaacaag aacaaattgc aagacagcag cagcagcttc    2760
tacagcaaca acacaaaatc aatttgctcc agcaacagat ccaggttcaa ggtcagctgc    2820
cgccattaat gattcccgta ttccctcctg atcaacggac actggctgca gctgcccagc    2880
aaggattcct cctccctcca ggcttcagct ataaggctgg atgtagtgac ccttaccctg    2940
ttcagctgat cccaactacc atggcagctg ctgccgcagc aacaccaggc ttaggcccac    3000
tccaactgca gcagttatat gctgcccagc tagctgcaat gcaggtatct ccaggaggga    3060
agctgccagg catacccaa ggcaaccttg gtgctgctgt atctcctacc agcattcaca    3120
cagacaagag cacaaacagc ccaccaccca aaagcaagga aaaacaaca ctggagagtc    3180 tgactcagca actggcagtt aaacagaatg aagaaggaaa atttagccat gcaatgatgg    3240
atttcaatct gagtggagat tctgatggaa gtgctggagt ctcagagtca agaatttata    3300
gggaatcccg agggcgtggt agcaatgaac cccacataaa gcgtccaatg aatgccttca    3360
tggtgtgggc taaagatgaa cggagaaaga tccttcaagc ctttcctgac atgcacaact    3420
ccaacatcag caagatattg ggatctcgct ggaaagctat gacaaaccta gagaaacagc    3480
catattatga ggagcaagcc cgtctcagca agcagcacct ggagaagtac cctgactata    3540
agtacaagcc caggccaaag cgcacctgcc tggtggatgg caaaaagctg cgcattggtg    3600
aatacaaggc aatcatgcgc aacaggcggc aggaaatgcg gcagtacttc aatgttgggc    3660
aacaagcaca gatccccatt gccactgctg gtgttgtgta ccctggagcc atcgccatgg    3720
ctgggatgcc ctcccctcac ctgccctcgg agcactcaag cgtgtctagc agcccagagc    3780
ctgggatgcc tgttatccag agcacttacg gtgtgaaagg agaggagcca catatcaaag    3840
aagagataca ggccgaggac atcaatggag aaatttatga tgagtacgac gaggaagagg    3900
atgatccaga tgtagattat gggagtgaca gtgaaaacca tattgcagga caagccaacg    3960
agggcagagg aagtcttcta acatgcggtg acgtggagga gaatcccggc cctatttaaa    4020
tgtcttccaa gcaagccacc tctccatttg cctgtgcagc tgatggagag gatgcaatga    4080
cccaggattt aacctcaagg gaaaaggaag agggcagtga tcaacatgtg gcctcccatc    4140
tgcctctgca ccccataatg cacaacaaac ctcactctga ggagctacca acacttgtca    4200
gtaccattca acaagatgct gactgggaca gcgttctgtc atctcagcaa agaatggaat    4260
cagagaataa taagttatgt tccctatatt ccttccgaaa tacctctacc tcaccacata    4320
agcctgacga agggagtcgg gaccgtgaga taatgaccag tgttactttt ggaaccccag    4380
```

```
agcgccgcaa agggagtctt gccgatgtgg tggacacact gaaacagaag aagcttgagg    4440
aaatgactcg gactgaacaa gaggattcct cctgcatgga aaaactactt tcaaaagatt    4500
ggaaggaaaa aatggaaaga ctaaatacca gtgaacttct tggagaaatt aaaggtacac    4560
ctgagagcct ggcagaaaaa gaacggcagc tctccaccat gattacccag ctgatcagtt    4620
tacgggagca gctactggca gcgcatgatg aacagaaaaa actggcagcg tcacaaattg    4680
agaaacaacg gcagcaaatg gaccttgctc gccaacagca gaacagatt gcgagacaac    4740 agcagcaact tctgcaacag cagcacaaaa ttaatctcct gcagcaacag atccaggttc    4800
agggtcacat gcctccgctc atgatcccaa ttttttccaca tgaccagcgg accctggcag    4860
cagctgctgc tgcccaacag ggattcctct tcccccctgg aataacatac aaaccaggtg    4920
ataactaccc cgtacagttc attccatcaa caatggcagc tgctgctgct tctggactca    4980 gcccttttaca gctccagaag ggtcatgtct cccacccaca aattaaccaa aggctaaagg    5040
gcctaagtga ccgttttggc aggaatttgg acacctttga acatggtggt ggccactctt    5100
acaaccacaa acagattgag cagctctatg ccgctcagct ggccagcatg caggtgtcac    5160
ctggagcaaa gatgccatca actccacagc caccaaacac agcagggacg gtctcacccta   5220 ctgggataaa aaatgaaaag agagggacca gccctgtaac tcaagttaag gatgaagcag    5280
cagcacagcc tctgaatctc tcatcccgac ccaagacagc agagcctgta aagtccccaa    5340
cgtctcccac ccagaacctc ttcccagcca gcaaaaccag ccctgtcaat ctgccaaaca    5400
aaagcagcat ccctagcccc attggaggaa gcctgggaag aggatcctct ttagatatcc    5460
tatctagtct caactcccct gcccttttttg gggatcagga tacagtgatg aaagccattc    5520
aggaggcgcg gaagatgcga gagcagatcc agcgggagca acagcagcaa cagccacatg    5580
gtgttgacgg gaaactgtcc tccataaata atatgggggct gaacagctgc aggaatgaaa    5640
aggaaagaac gcgctttgag aatttggggc cccagttaac gggaaagtca atgaagatg     5700 gaaaactggg cccaggtgtc atcgaccta ctcggccaga agatgcagag ggaagtaaag     5760
caatgaatgg ctctgcagct aaactacagc agtattattg ttggccaaca ggaggtgcca    5820
ctgtggctga agcacgagtc tacagggacg cccgcggccg tgccagcagc gagccacaca    5880
ttaagcgacc aatgaatgca ttcatggttt gggcaaagga tgagaggaga aaaatccttc    5940
aggccttccc cgacatgcat aactccaaca ttagcaaaat cttaggatct cgctggaaat    6000
caatgtccaa ccaggagaag caaccttatt atgaagagca ggcccggcta agcaagatcc    6060
acttagagaa gtacccaaac tataaataca aaccccgacc gaaacgcacc tgcattgttg    6120
atggcaaaaa gcttcggatt ggggagtata agcaactgat gaggtctcgg agacaggaga    6180
tgaggcagtt ctttactgtg gggcaacagc ctcagattcc aatcaccaca ggaacaggtg    6240
ttgtgtatcc tggtgctatc actatggcaa ctaccacacc atcgcctcag atgacatctg    6300
actgctctag cacctcggcc agccggagc ccagcctccc ggtcatccag agcacttatg     6360
gtatgaagac agatggcgga agcctagctg gaaatgaaat gatcaatgga gaggatgaaa    6420
tggaaatgta tgatgactat gaagatgacc ccaaatcaga ctatagcagt gaaaatgaag    6480 cccggaggc tgtcagtgcc aactgagtcg caatcaacc tctgattaca aaatttgtga     6540
aagattgact ggtattctta actatgttgc tccttttacg ctatgtggat acgctgcttt    6600
aatgcctttg tatcatgcta ttgcttcccg tatggctttc attttctcct ccttgtataa    6660
atcctggttc ctgtctcttt atgaggagtt gtggcccgtt gtcaggcaac gtggcgtggt    6720
gtgcactgtg tttgctgacg caacccccac tggttggggc attgccacca cctgtcagct    6780
```

-continued

```
cctttccggg actttcgctt tcccctccc tattgccacg gcggaactca tcgccgcctg    6840
ccttgcccgc tgctggacag gggctcggct gttgggcact gacaattccg tggtgttgtc    6900
ggggaaatca tcgtcctttc cttggctgct cgcctgtgtt gccacctgga ttctgcgcgg    6960
gacgtccttc tgctacgtcc cttcggccct caatccagcg gaccttcctt cccgcgccct    7020
gctgccggct ctgcggcctc ttccgcgtct tcgccttcgc cctcagacga gtcggatctc    7080
cctttgggcc gcctccccgc ctggtacctt taagaccaat gacttacaag gcagctgtag    7140
atcttagcca cttttaaaa gaaaggggg gactggaagg gctaattcac tcccaacgaa    7200
gataagatct gcttttgct tgtactgggt ctctctggtt agaccagatc tgagcctggg    7260
agctctctgg ctaactaggg aacccactgc ttaagcctca ataaagcttg ccttgagtgc    7320
ttcaagtagt gtgtgcccgt ctgttgtgtg actctggtaa ctagagatcc ctcagaccct    7380
tttagtcagt gtggaaaatc tctagcagta gtagttcatg tcatcttatt attcagtatt    7440
tataacttgc aaagaaatga atatcagaga gtgagaggaa cttgtttatt gcagcttata    7500
atggttacaa ataaagcaat agcatcacaa atttcacaaa taaagcattt ttttcactgc    7560
attctagttg tggtttgtcc aaactcatca atgtatctta tcatgtctgg ctctagctat    7620
cccgccccta actccgccca tcccgcccct aactccgccc agttccgccc attctccgcc    7680
ccatggctga ctaattttt ttattatgc agaggccgag gccgcctcgg cctctgagct    7740
attccagaag tagtgaggag gcttttttgg aggcctagac ttttgcagat cgacccatgg    7800
gggcccgccc caactggggt aacctttgag ttctctcagt tgggggg          7846
```

<210> SEQ ID NO 2
<211> LENGTH: 5824
<212> TYPE: DNA
<213> ORGANISM: Artificial
<220> FEATURE:
<223> OTHER INFORMATION: MC/SOX-Duo

<400> SEQUENCE: 2

```
tgccagggcg tgcccttggg ctccccgggc gcgactagtg aattgatact agtattatgc      60
ccagtacatg accttatggg actttcctac ttggcagtac atctacgtat tagtcatcgc     120
tattaccatg gtgatgcggt tttggcagta catcaatggg cgtggatagc ggtttgactc     180
acggggattt ccaagtctcc accccattga cgtcaatggg agtttgtttt ggcaccaaaa     240
tcaacgggac tttccaaaat gtcgtaacaa ctccgcccca ttgacgcaaa tgggcggtag     300
gcgtgtacgg tgggaggttt atataagcag agctcgttta gtgaaccgtc agatcgcctg     360
gagacgccat ccacgctgtt ttgacctcca tagaagattc tagagccacc atgaatctcc     420 tggaccccctt catgaagatg accgacgagc aggagaaggg cctgtccggc gccccagcc     480 ccaccatgtc cgaggactcc gcgggctcgc cctgcccgtc gggctccggc tcggacaccg     540
agaacacgcg gccccaggag aacacgttcc caaggggcga gccgatctg aagaaggaga     600 gcgaggagga caagttcccc gtgtgcatcc gcgaggcggt cagccaggtg ctcaaaggct     660
acgactggac gctggtgccc atgccggtgc gcgtcaacgg ctccagcaag aacaagccgc     720
acgtcaagcg gcccatgaac gccttcatgg tgtgggcgca ggcggcgcgc aggaagctcg     780
cggaccagta cccgcacttg cacaacgccg agctcagcaa gacgctgggc aagctctgga     840
gacttctgaa cgagagcgag aagcggcct tcgtggagga ggcggagcgg ctgcgcgtgc     900
agcacaagaa ggaccacccg gattacaagt accagccgcg gcggaggaag tcggtgaaga     960
```

```
acgggcaggc ggaggcagag gaggccacgg agcagacgca catctccccc aacgccatct    1020
tcaaggcgct gcaggccgac tcgccacact cctcctccgg catgagcgag gtgcactccc    1080
ccggcgagca ctcggggcaa tcccagggcc caccgacccc acccaccacc cccaaaaccg    1140
acgtgcagcc gggcaaggct gacctgaagc gagaggggcg ccccttgcca gagggggca    1200 gacagccccc tatcgacttc cgcgacgtgg acatcggcga gctgagcagc gacgtcatct    1260
ccaacatcga gaccttcgat gtcaacgagt ttgaccagta cctgccgccc aacgccacc    1320 cggggggtgcc ggccacgcac ggccaggtca cctacacggg cagctacggc atcagcagca    1380
ccgcggccac cccggcgagc gcgggccacg tgtggatgtc caagcagcag gcgccgccgc    1440
cacccccgca gcagccccca caggccccgc cggccccgca ggcgccccg cagccgcagg    1500 cggcgccccc acagcagccg gcggcacccc cgcagcagcc acaggcgcac acgctgacca    1560
cgctgagcag cgagccgggc cagtcccagc gaacgcacat caagacggag cagctgagcc    1620
ccagccacta cagcgagcag cagcagcact cgccccaaca gatcgcctac agccccttca    1680
acctcccaca ctacagcccc tcctacccgc ccatcacccg ctcacagtac gactacaccg    1740
accaccagaa ctccagctcc tactacagcc acgcggcagg ccagggcacc ggcctctact    1800
ccaccttcac ctacatgaac cccgctcagc gccccatgta caccccatc gccgacacct    1860 ctggggtccc ttccatcccg cagacccaca gcccccagca ctgggaacaa cccgtctaca    1920
cacagctcac tcgacctgag ggcagaggaa gtcttctaac atgcggtgac gtggaggaga    1980
atcccggccc tgaattcatg tcttccaagc aagccacctc tccatttgcc tgtgcagctg    2040
atggagagga tgcaatgacc caggatttaa cctcaaggga aaaggaagag ggcagtgatc    2100
aacatgtggc ctcccatctg cctctgcacc ccataatgca caacaaacct cactctgagg    2160
agctaccaac acttgtcagt accattcaac aagatgctga ctgggacagc gttctgtcat    2220
ctcagcaaag aatggaatca gagaataata agttatgttc cctatattcc ttccgaaata    2280
cctctacctc accacataag cctgacgaag ggagtcggga ccgtgagata atgaccagtg    2340
ttacttttgg aaccccagag cgccgcaaag ggagtcttgc cgatgtggtg gacacactga    2400
aacagaagaa gcttgaggaa atgactcgga ctgaacaaga ggattcctcc tgcatggaaa    2460
aactactttc aaaagattgg aaggaaaaa tggaaagact aaataccagt gaacttcttg    2520
gagaaattaa aggtacacct gagagcctgg cagaaaaga acggcagctc tccaccatga    2580
ttacccagct gatcagttta cgggagcagc tactggcagc gcatgatgaa cagaaaaaac    2640
tggcagcgtc acaaattgag aaacaacggc agcaaatgga ccttgctcgc caacagcaag    2700
aacagattgc gagacaacag cagcaacttc tgcaacagca gcacaaaatt aatctcctgc    2760
agcaacagat ccaggttcag ggtcacatgc ctccgctcat gatcccaatt tttccacatg    2820
accagcggac cctggcagca gctgctgctg cccaacaggg attcctcttc cccctggaa    2880 taacatacaa accaggtgat aactacccg tacagttcat tccatcaaca atggcagctg    2940
ctgctgcttc tggactcagc cctttacagc tccagaaggg tcatgtctcc cacccacaaa    3000
ttaaccaaag gctaagggc ctaagtgacc gttttggcag gaatttggac acctttgaac    3060
atggtggtgg ccactcttac aaccacaaac agattgagca gctctatgcc gctcagctgg    3120
ccagcatgca ggtgtcacct ggagcaaaga tgccatcaac tccacagcca ccaaacacag    3180
cagggacggt ctcacctact gggataaaaa atgaaaagag agggaccagc cctgtaactc    3240
aagttaagga tgaagcagca gcacagcctc tgaatctctc atcccgaccc aagacagcag    3300
agcctgtaaa gtccccaacg tctcccaccc agaacctctt cccagccagc aaaaccagcc    3360
```

```
ctgtcaatct gccaaacaaa agcagcatcc ctagccccat tggaggaagc ctgggaagag    3420
gatcctcttt agatatccta tctagtctca actcccctgc ccttttggg gatcaggata     3480 cagtgatgaa agccattcag gaggcgcgga agatgcgaga gcagatccag cgggagcaac    3540
agcagcaaca gccacatggt gttgacggga aactgtcctc cataaataat atggggctga    3600
acagctgcag gaatgaaaag gaaagaacgc gctttgagaa tttggggccc cagttaacgg    3660
gaaagtcaaa tgaagatgga aaactgggcc caggtgtcat cgaccttact cggccagaag    3720
atgcagaggg aagtaaagca atgaatggct ctgcagctaa actacagcag tattattgtt    3780
ggccaacagg aggtgccact gtggctgaag cacgagtcta cagggacgcc cgcggccgtg    3840
ccagcagcga gccacacatt aagcgaccaa tgaatgcatt catggtttgg gcaaaggatg    3900
agaggagaaa aatccttcag gccttccccg acatgcataa ctccaacatt agcaaaatct    3960
taggatctcg ctggaaatca atgtccaacc aggagaagca accttattat gaagagcagg    4020
cccggctaag caagatccac ttagagaagt acccaaacta taaatacaaa ccccgaccga    4080
aacgcacctg cattgttgat ggcaaaaagc ttcggattgg ggagtataag caactgatga    4140
ggtctcggag acaggagatg aggcagttct ttactgtggg gcaacagcct cagattccaa    4200
tcaccacagg aacaggtgtt gtgtatcctg gtgctatcac tatggcaact accacaccat    4260
cgcctcagat gacatctgac tgctctagca cctcggccag cccggagccc agcctcccgg    4320
tcatccagag cacttatggt atgaagacag atggcggaag cctagctgga aatgaaatga    4380
tcaatggaga ggatgaaatg gaaatgtatg atgactatga agatgacccc aaatcagact    4440
atagcagtga aaatgaagcc ccggaggctg tcagtgccaa ctgagtcgac aatcaacctc    4500
tgattacaaa atttgtgaaa gattgactgg tattcttaac tatgttgctc cttttacgct    4560
atgtggatac gctgctttaa tgcctttgta tcatgctatt gcttcccgta tggctttcat    4620
tttctcctcc ttgtataaat cctggttgct gtctctttat gaggagttgt ggcccgttgt    4680
caggcaacgt ggcgtggtgt gcactgtgtt tgctgacgca acccccactg gttggggcat    4740
tgccaccacc tgtcagctcc tttccgggac tttcgctttc ccctcccta ttgccacggc     4800 ggaactcatc gccgcctgcc ttgcccgctg ctggacaggg gctcggctgt tgggcactga    4860
caattccgtg tgtgttgtcgg ggaaatcatc gtccttcct tggctgctcg cctgtgttgc    4920
cacctggatt ctgcgcggga cgtccttctg ctacgtccct tcggccctca atccagcgga    4980
ccttccttcc cgcgccctgc tgccggctct gcggcctctt ccgcgtcttc gccttcgccc    5040
tcagacgagt cggatctccc tttgggccgc ctccccgcct ggtaccttta agaccaatga    5100
cttacaaggc agctgtagat cttagccact tttaaaaga aaggggggga ctggaagggc     5160
taattcactc ccaacgaaga taagatctgc tttttgcttg tactgggtct ctctggttag    5220
accagatctg agcctgggag ctctctggct aactagggaa cccactgctt aagcctcaat    5280
aaagcttgcc ttgagtgctt caagtagtgt gtgcccgtct gttgtgtgac tctggtaact    5340
agagatccct cagaccecttt tagtcagtgt ggaaaatctc tagcagtagt agttcatgtc    5400
atcttattat tcagtattta taacttgcaa agaaatgaat atcagagagt gagaggaact    5460
tgtttattgc agcttataat ggttacaaat aaagcaatag catcacaaat ttcacaaata    5520
aagcattttt ttcactgcat tctagttgtg gtttgtccaa actcatcaat gtatcttatc    5580
atgtctggct ctagctatcc cgcccctaac tccgcccatc ccgcccctaa ctccgcccag    5640
ttccgcccat tctccgcccc atggctgact aatttttttt atttatgcag aggccgaggc    5700
```

```
cgcctcggcc tctgagctat tccagaagta gtgaggaggc ttttttggag gcctagactt    5760
ttgcagatcg acccatgggg gcccgcccca actggggtaa cctttgagtt ctctcagttg    5820
gggg                                                                 5824
```

<210> SEQ ID NO 3
<211> LENGTH: 34
<212> TYPE: DNA
<213> ORGANISM: Artificial
<220> FEATURE:
<223> OTHER INFORMATION: SOX9-E2A-XbaI_Forward

<400> SEQUENCE: 3

```
tctagagcca ccatgaatct cctggacccc ttca                                34
```

<210> SEQ ID NO 4
<211> LENGTH: 108
<212> TYPE: DNA
<213> ORGANISM: Artificial
<220> FEATURE:
<223> OTHER INFORMATION: SOX9-E2A-EcoRI_Reverse

<400> SEQUENCE: 4

```
gaattcagga ccggggttat tactttcaac atcgccagcg agtttcaaca aagcgtagtt    60
agtacattga cccgacccgt tgaatgcat aggtcgagtg agctgtgt                 108
```

<210> SEQ ID NO 5
<211> LENGTH: 25
<212> TYPE: DNA
<213> ORGANISM: Artificial
<220> FEATURE:
<223> OTHER INFORMATION: SOX5-T2A-EcoRI_Forward

<400> SEQUENCE: 5

```
gaattcatgt cttccaagcg accag                                          25
```

<210> SEQ ID NO 6
<211> LENGTH: 81
<212> TYPE: DNA
<213> ORGANISM: Artificial
<220> FEATURE:
<223> OTHER INFORMATION: SOX5-T2A-SwaI_Reverse

<400> SEQUENCE: 6

```
atttaaatag ggccgggatt ctcctccacg tcaccgcatg ttagaagact tcctctgccc    60
tcgttggctt gtcctgcaat a                                              81
```

<210> SEQ ID NO 7
<211> LENGTH: 25
<212> TYPE: DNA
<213> ORGANISM: Artificial
<220> FEATURE:
<223> OTHER INFORMATION: SOX6-SwaI_Forward

<400> SEQUENCE: 7

```
atttaaatgt cttccaagca agcca                                          25
```

<210> SEQ ID NO 8
<211> LENGTH: 24
<212> TYPE: DNA
<213> ORGANISM: Artificial
<220> FEATURE:
<223> OTHER INFORMATION: SOX6-SalI_Reverse

<400> SEQUENCE: 8

```
gtcgactcag ttggcactga cagc                                              24

<210> SEQ ID NO 9
<211> LENGTH: 81
<212> TYPE: DNA
<213> ORGANISM: Artificial
<220> FEATURE:
<223> OTHER INFORMATION: SOX9-T2A-EcoRI_Reverse

<400> SEQUENCE: 9
gaattcaggg ccgggattct cctccacgtc accgcatgtt agaagacttc ctctgccctc       60
aggtcgagtg agctgtgtgt a                                                 81

<210> SEQ ID NO 10
<211> LENGTH: 25
<212> TYPE: DNA
<213> ORGANISM: Artificial
<220> FEATURE:
<223> OTHER INFORMATION: SOX6-EcoRI_Forward

<400> SEQUENCE: 10
gaattcatgt cttccaagca agcca                                             25

<210> SEQ ID NO 11
<211> LENGTH: 84
<212> TYPE: DNA
<213> ORGANISM: Artificial
<220> FEATURE:
<223> OTHER INFORMATION: E2A

<400> SEQUENCE: 11
atgcattcaa acgggtcggg tcaatgtact aactacgctt tgttgaaact cgctggcgat       60
gttgaaagta ataaccccgg tcct                                              84

<210> SEQ ID NO 12
<211> LENGTH: 54
<212> TYPE: DNA
<213> ORGANISM: Artificial
<220> FEATURE:
<223> OTHER INFORMATION: T2A

<400> SEQUENCE: 12
gagggcagag gaagtcttct aacatgcggt gacgtggagg agaatcccgg ccct             54
```

NONVIRAL MINICIRCLE VECTOR CARRYING SOX GENE AND CONSTRUCTION METHOD THEREFOR

CROSS REFERENCE TO RELATED APPLICATIONS

This application is a 35 U.S.C. § 371 national stage application of PCT International Application No. PCT/KR2017/006328, filed Jun. 16, 2017, which claims priority from Korean Patent Application No. 10-2016-0101761, filed Aug. 10, 2016, the contents of which are incorporated herein by reference in their entireties. The above-referenced PCT International Application was published in the Korean language as International Publication No. WO 2018/030630 A1 on Feb. 15, 2018.

STATEMENT REGARDING ELECTRONIC FILING OF A SEQUENCE LISTING

A Sequence Listing in ASCII text format, submitted under 37 C.F.R. § 1.821, entitled 1433-16 ST25.txt, 20,634 bytes in size, generated on Mar. 8, 2019 and filed via EFS-Web, is provided in lieu of a paper copy. This Sequence Listing is incorporated by reference into the specification for its disclosures.

TECHNICAL FIELD

The present invention relates to a non-viral minicircle vector expressing a SOX gene, a stem cell into which the vector is introduced, a pharmaceutical composition for preventing or treating a cartilage disease, including the stem cell, and a method for constructing the vector.

BACKGROUND ART

When once damaged, articular cartilage cannot be regenerated into original tissue, and it is difficult to heal the damaged articular cartilage, so that various attempts have been made to solve the problem. Currently, for advanced degenerative arthritis, it has been established as a standard treatment to remove the affected cartilage and bone and replace them with an artificial joint consisting of a metal and polyethylene, but the life time of such an artificial joint becomes an issue when the artificial joint is implanted into a relatively young patient in his/her 60's or younger.

In order to solve the aforementioned problems, an attempt to isolate and culture chondrocytes collected from sites other than a weight bearing surface and self-transplant the chondrocytes into the cartilage defect site was conducted on a human for the first time in 1994 by Professor Peterson of the Gothenburg University Hospital in Sweden and presently is now being widely conducted, but this method still has problems such as a problem in that a part of normal tissues need to be sacrificed in order to collect autologous cartilage, a reproducibility problem in that transplanted cells are not positioned in proper locations and leak out, a doubt as to whether a proper function as a complete cartilage can be served in the long term, and a problem in that chondrocytes are not proliferated well in a patient with degenerative arthritis, who is a subject to whom the method is actually applied. In order to solve these problems, stem cells having advantages in that stem cells have the ability to self-replicate and can differentiate into various tissues, and a large amount of stem cells can be easily collected without dysfunction of a donor site have been recently recognized as an ideal cell source for cell therapy, and thus studies on stem cells have been actively conducted (Korean Patent No. 10-1287861). However, there is still a lack of clear knowledge on factors, environment, and the like for forming cartilage.

Adult stem cells can be obtained from the patient's own body, and thus are free from ethical problems concerning the acquisition of cells, which are of recent interest, and can differentiate into each connective tissue such as bone, cartilage, fat, muscle, and tendon according to the ability to self-replicate and the culture conditions, and thus have been recognized as a very useful cell source for regeneration of musculoskeletal tissues. In most of the studies on adult stem cells conducted until now, mesenchymal stem cells extracted from bone marrow and cultured have been used, and it is known that adult stem cells are present even in most of the musculoskeletal tissues such as periosteum, adipose tissue, and muscle in addition to the mesenchymal stem cells. In particular, adipose tissue can be easily obtained in a large amount without dysfunction of a donor site by using a relatively simple liposuction, and thus has recently drawn attention as a supply source for adult stem cells. Various studies have revealed that bone marrow cells as well as adipose tissues originate from the embryonic mesoderm and adult stem cells isolated from fat may differentiate into bone or cartilage. However, despite the aforementioned advantages, the low differentiation capacity of adipose stem cells has been regarded as a limitation for use as a cell source of adipose stem cells. Accordingly, in order to use adipose stem cells as a useful cell source, discovery of various factors affecting the differentiation of adipose stem cells and intensive studies thereon need to precede anything else.

The most studied method until now to improve the function of adult stem cells is a genetic manipulation technique. That is, the method is to improve the function of adult stem cells by inserting a specific gene into the adult stem cells so as to increase the secretion of various differentiation-inducing factors. Many study results in the related art have reported that a case where adult stem cells into which a gene is inserted are transplanted into the corresponding animal model may have even better therapeutic effects than a case where adult stem cells into which a gene is not inserted are transplanted into the animal model. However, since viruses have been used until now for the manipulation of genes and adult stem cells genetically manipulated by using viruses cannot be used clinically yet due to safety issues, there remains a problem to be overcome. Therefore, various studies trying to manipulate genes without using viruses have been conducted.

SUMMARY OF THE INVENTION

The present invention has been made in an effort to construct a non-viral minicircle vector to which a SOX gene (SOX5, SOX6, or SOX9) is transferred in order to solve the aforementioned problems in the related art, and more specifically, the present inventors constructed a vector which adopts, as a backbone, a minicircle vector in which an unnecessary bacterial backbone is automatically removed in the process of constructing a vector so as to be clinically applied in the construction of the aforementioned vector, in which the expression of three SOX genes (SOX5, SOX6, and SOX9) or two SOX genes (SOX6 and SOX9) is simultaneously regulated under one promoter.

The present inventors confirmed that each recombinant protein was successfully expressed in the vector, and that when stem cells were transformed by introducing the vector into the stem cells, the chondrogenic differentiation efficiency was effectively enhanced.

Thus, an object of the present invention is to provide a non-viral minicircle vector to which a SOX gene (SOX5, SOX6, or SOX9) is transferred.

Another object of the present invention is to provide a stem cell into which the vector is introduced.

Still another object of the present invention is to provide a pharmaceutical composition for preventing or treating a cartilage disease, including the stem cell as an active ingredient.

Yet another object of the present invention is to provide a method for constructing a non-viral minicircle vector to which a SOX gene is transferred.

However, a technical problem to be achieved by the present invention is not limited to the aforementioned problem, and the other problems that are not mentioned may be clearly understood by a person skilled in the art from the following description.

An exemplary embodiment of the present invention provides a non-viral minicircle vector including:
(a) a promoter;
(b) a gene encoding two or more proteins selected from the group consisting of SRY (sex determining region Y)-box 5 (SOX5), SRY-box 6 (SOX6), and SRY-box 9 (SOX9); and
(c) a gene expression cassette consisting of a terminator,
in which the non-viral minicircle vector does not include
(d) a bacterial backbone.

As an exemplary embodiment of the present invention, the vector may sequentially include a SOX9 gene, a SOX5 gene, and a SOX6 gene.

As another exemplary embodiment of the present invention, the vector may sequentially include a SOX9 gene and a SOX6 gene.

As still another exemplary embodiment of the present invention, the vector sequentially including the SOX9 gene, the SOX5 gene, and the SOX6 gene may consist of a base sequence of SEQ ID NO: 1.

As yet another exemplary embodiment of the present invention, the vector sequentially including the SOX9 gene and the SOX6 gene may consist of a base sequence of SEQ ID NO: 2.

As still yet another exemplary embodiment of the present invention, the promoter may be a cytomegalovirus (CMV).

As a further exemplary embodiment of the present invention, the terminator may include an SV40 polyadenylation sequence.

As another further exemplary embodiment of the present invention, the vector may be a double-stranded DNA in a circular supercoiled form.

Yet another exemplary embodiment provides a stem cell into which the non-viral minicircle vector is introduced.

As an exemplary embodiment of the present invention, the stem cell may be an adult stem cell.

Still another exemplary embodiment provides a stem cell into which the non-viral minicircle vector is introduced.

As an exemplary embodiment of the present invention, the stem cell may be an adult stem cell.

Still yet another exemplary embodiment provides a pharmaceutical composition for preventing or treating a cartilage disease, including the stem cell as an active ingredient.

As an exemplary embodiment of the present invention, the cartilage disease may be degenerative arthritis, rheumatic arthritis, ankylosing spondylitis, posttraumatic arthritis, osteochondritis dissencans, or osteomalacia.

As another exemplary embodiment of the present invention, the composition may promote the differentiation of stem cells into chondrocytes.

A further exemplary embodiment provides a method for constructing a non-viral minicircle vector to which a SOX gene is transferred, the method including the following steps:
(a) constructing a parental plasmid to which SOX genes are transferred by sequentially transferring and connecting three or two SRY (sex determining region Y)-box (SOX) genes to a parental plasmid;
(b) introducing the constructed parental plasmid into *E. coli*; and
(c) obtaining a non-viral minicircle vector for expressing a SOX gene from which a bacterial backbone vector is removed by treating a culture solution of *E. coli* into which the parental plasmid is introduced with arabinose.

As an exemplary embodiment of the present invention, the three or two SOX genes in step (a) may be SOX9, SOX5, and SOX6; and SOX9 and SOX6, respectively.

As another exemplary embodiment of the present invention, the *E. coli* in step (b) may be an *E. coli* simultaneously expressing a ΦC31 integrase and an I-SceI endonuclease.

Another further exemplary embodiment provides a method for preventing or treating a cartilage disease, the method including: administering a pharmaceutical composition including the stem cell as an active ingredient to an individual.

Still another further exemplary embodiment provides a use of the stem cell for preventing or treating a cartilage disease.

The transformation of mesenchymal stem cells with MC/SOX-Trio or MC/SOX-Duo, which is a non-viral minicircle vector to which a SOX gene is transferred according to the present invention, can completely exclude the necessity of expensive growth factors that have been indispensably used in inducing the differentiation of mesenchymal stem cells into chondrocytes. Accordingly, the mesenchymal stem cells transformed therewith, when implanted in vivo, can differentiate into chondrocytes by themselves, and thus have an advantage capable of simplifying the existing complicated steps of culturing cells to induce differentiation and then transplanting the cells.

Unlike existing vector systems in which antibiotic-resistant genes and other bacteria-derived exogenous genes are simultaneously transferred to cells even after transformation, the vector of the present invention minimizes transfer of unnecessary genes into target cells by allowing two or three SOX genes necessary only for differentiation into chondrocytes to be regulated under one promoter, and thus can be utilized as a non-viral vector system in the most advantageous form for use in clinical application of stem cell-gene therapeutic agents.

BRIEF DESCRIPTION OF THE DRAWINGS

FIG. 1 illustrates a process of constructing a minicircle vector including only an exogenous gene having no bacterial backbone vector from a parental plasmid with a drawing.

FIG. 2 illustrates structures of a pMC/SOX-trio vector in which three SOX genes (SOX9, SOX5, and SOX6) are transferred to a parental plasmid and a pMC/SOX-duo vector in which two SOX genes (SOX9 and SOX6) are transferred to a parental plasmid according to the present invention with a drawing.

FIG. 3 is a result that the vectors are cut by each restriction enzyme and then electrophoresis is performed in order to confirm the transfer of the SOX genes to the pMC/SOX-trio and pMC/SOX-duo vectors.

FIG. 4 is a result that electrophoresis is performed in order to confirm whether a minicircle vector is constructed after the pMC/SOX-trio and pMC/SOX-duo vectors are introduced into *E. coli* and treated with 0.5% arabinose.

FIG. 5 is a result that the expression levels of mRNAs of SOX6 and SOX9 are measured in adipose stem cells transformed with a SOX-duo minicircle DNA.

FIG. 6 is a result that the expression levels of proteins of SOX6 and SOX9 are measured in adipose stem cells transformed with a SOX-duo minicircle DNA.

FIG. 7 is a result that the size of a chondrogenic differentiation pellet is measured after adipose stem cells transformed with a SOX-trio or SOX-duo minicircle DNA are cultured for 3 weeks.

FIG. 8 is a result that the expression levels of mRNAs of SOX9, Type II collagen (COLII), and Aggrecan in a chondrogenic differentiation pellet are measured after adipose stem cells transformed with a SOX-trio or SOX-duo minicircle DNA are cultured for 3 weeks.

FIG. 9 is a result that the degree of chondrogenic differentiation is confirmed by subjecting chondrogenic pellet tissues to Safranin-O staining after adipose stem cells transformed with a SOX-trio or SOX-duo minicircle DNA are cultured for 3 weeks.

DETAILED DESCRIPTION

The present invention relates to a non-viral minicircle vector to which a SOX gene is transferred, a stem cell into which the vector is introduced, a pharmaceutical composition for preventing or treating a cartilage disease, including the stem cell, and a method for constructing the vector.

Hereinafter, the present invention will be described in more detail.

The present invention provides a non-viral minicircle vector including:
(a) a promoter;
(b) a gene encoding two or more proteins selected from the group consisting of SRY (sex determining region Y)-box 5 (SOX5), SRY-box 6 (SOX6), and SRY-box 9 (SOX9); and
(c) a gene expression cassette consisting of a terminator, in which the non-viral minicircle vector does not include
(d) a bacterial backbone.

In order to solve all the problems of the biological stability such as immunogenicity possessed by a viral vector system conventionally used in the gene therapy method and the transfer efficiency possessed by a non-viral vector system in the present invention, a highly safe vector system capable of efficiently delivering a therapeutic gene to a target cell and expressing the gene sustainably for a long period of time was developed.

Specifically, the vector system of the present invention includes a promoter, a gene encoding a SOX protein, and a gene expression cassette consisting only of a minimum essential component such as a transcription terminator, and does not include a bacterial backbone including a selectable marker gene such as an origin of replication and an antibiotic resistance gene used in an existing vector system.

Since an origin of replication may usually cause an unnecessary immune response in the human body as a sequence derived from bacteria and a selectable marker gene such as an antibiotic resistance gene may be delivered even to bacteria present in the body, there is a problem in that the administration of a therapeutic antibiotic of the same group due to other diseases may cause unnecessary antibiotic resistance. Thus, the present invention does not include an origin of replication and a selectable marker gene, thereby eliminating the problems of unnecessary immune response and antibiotic resistance. In addition, the immune response can be reduced by removing unmethylated CpG motifs derived from prokaryotic cells. Furthermore, accordingly, the vector of the present invention has a smaller physical size than the existing vector, and thus may be easily constructed, increase the delivery efficiency, and improve the biological stability.

Thus, in the Examples of the present invention, it was confirmed that polycistronic and bicistronic vectors in which the expression of three or two SOX genes are regulated to be simultaneously expressed under one promoter were constructed by using the vector system, and the chondrogenic differentiation induction efficiency was enhanced by introducing the vectors into stem cells.

In an Example of the present invention, two 2A (E2A and T2A) systems are introduced into a parental plasmid vector such that three SOX genes (SOX9, SOX5, and SOX6) or two SOX genes (SOX9 and SOX6) can be simultaneously expressed to sequentially connect the genes in descending order of size, thereby constructing a pMC/SOX-trio vector to which SOX9, SOX5, and SOX6 genes are transferred and a pMC/SOX-duo vector to which SOX9 and SOX6 genes are transferred (see Example 1).

In another Example of the present invention, it was confirmed through electrophoresis that each SOX gene was transferred well in the pMC/SOX-trio and pMC/SOX-duo vectors, and it was confirmed through electrophoresis that the vectors were introduced into *E. coli* and cultured and the culture solution was treated with 0.5% arabinose to construct a minicircle DNA from which a bacterial backbone vector is removed, that is, MC/SOX-trio and MC/SOX-duo vectors (see Example 2).

In still another Example of the present invention, in order to verify the chondrogenic differentiation efficiency by the minicircle DNA constructed in the above Example, adipose stem cells were transformed by introducing the DNA into adipose stem cells and cultured for 3 weeks, and then based on the form of a chondrogenic pellet, the expression levels of mRNAs of SOX9, Type II collagen (COLII), and Aggrecan in the pellet, and a chondrogenic pellet tissue analysis by Safranin-O staining, it was confirmed that the chodrogenic differentiation could be promoted with high efficiency only by transformation caused by a minicircle DNA to which the SOX gene was transferred without a separate growth factor treatment (see Example 3).

Accordingly, each of the non-viral MC/SOX-trio vector and the MC/SOX-duo vector of the present invention promotes the chondrogenic differentiation with high efficiency, and thus can be usefully used in the clinical setting of a stem cell-gene therapeutic agent for treating a cartilage disease.

In the present invention, the non-viral MC/SOX-trio vector is characterized by consisting of a base sequence of SEQ ID NO: 1 and the MC/SOX-duo vector is characterized by consisting of a base sequence of SEQ ID NO: 2.

The vector of the present invention is characterized by being a double-stranded DNA in a circular supercoiled form.

A promoter used in the vector of the present invention may use a promoter used in the art without particular limitation, includes an inducible or constitutive promoter, and preferably, may use a cytomegalovirus (CMV) promoter.

A terminator used in the vector of the present invention may use a terminator used in the art without particular limitation, but preferably, may be a terminator including an SV40 polyadenylation sequence.

The vector of the present invention may additionally include a promoter, a gene (SOX5, SOX6, or SOX9) encoding a SOX protein as a therapeutic gene, and a site specific recombinant region outside a gene expression cassette consisting of a terminator, and the site specific recombination region refers to a region where a recombination may occur between two specific base sequences on a DNA, and a gene cloning method using the site specific recombinant region is useful as a gene manipulation method capable of replacing an existing method using a restriction enzyme and a ligase. Preferably, the site specific recombinant region in the present invention is an att attachment sequence derived from *E. coli* or bacteriophage lambda, a substrate sequence of attB or attP, or a hybrid sequence of attR or attL, and more preferably, may be attR.

As another aspect of the present invention, the present invention provides a stem cell into which the non-viral minicircle vector is introduced.

The term "stem cell" used in the present invention is an undifferentiated cell that has differentiation ability, but is not differentiated yet, and is characterized by having a function as a pluripotent cell that can be converted into any organ from primitive stage cells, and preferably, includes a germline stem cell, an embryonic stem cell, an induced pluripotent stem cell, and a multipotent adult stem cell isolated from a bone marrow and the like of an adult body, and the like.

In the present invention, the stem cell includes all the multipotent stem cells derived from an adult tissue such as an embryo or fetus, cord blood or an adult organ or bone marrow of a mammal, the skin or blood, includes a stem cell having a character similar to that of an embryonic stem cell, and more preferably, may be an adult stem cell including a mesenchymal stem cell, a hematopoietic stem cell, a neural stem cell, an adipose stem cell, and the like.

As still another aspect of the present invention, the present invention provides a pharmaceutical composition for preventing or treating a cartilage disease, including a stem cell into which the non-viral minicircle vector is introduced as an active ingredient.

The term "prevention" used in the present invention means all actions that suppress a cartilage disease or delay the onset of the cartilage disease by administering the pharmaceutical composition according to the present invention.

The term "treatment" used in the present invention means all actions that ameliorate or beneficially change symptoms caused by a cartilage disease by administering the pharmaceutical composition according to the present invention.

The term "cartilage disease" used in the present invention means a disease caused by dysfunction or damage of the cartilage, and the cartilage disease in the present invention includes a disease that can be alleviated or treated through chondrogenic differentiation of a transformed stem cell into which the non-viral minicircle vector according to the present invention is introduced, and more specifically, may be degenerative arthritis, rheumatic arthritis, ankylosing spondylitis, posttraumatic arthritis, osteochondritis dissencans, or osteomalacia, but is not limited thereto.

In the present invention, a vector expressing a SOX gene may be introduced into cells or tissues by a plurality of publicly known methods, for example, transient transfection, micro-injection, transduction, electroporation, DEAE dextran-mediated transfection, monovalent cationic liposome fusion, multivalent cationic liposome fusion, protoplast fusion, lipofectamine, naked DNA delivery, and the like, but the method is not limited thereto.

The stem cells according to the present invention are administered in a manner of direct implantation or migration to a desired tissue site, and thus can provide a therapeutic effect in such a manner to reconstitute or regenerate a functionally deficient site.

The pharmaceutical composition according to the present invention includes a non-viral minicircle vector to which a SOX gene is transferred as an active ingredient, and may include a pharmaceutically acceptable carrier. The pharmaceutically acceptable carrier is typically used in formulation, and includes saline, sterile water, Ringer's solution, buffered saline, cyclodextrin, a dextrose solution, a maltodextrin solution, glycerol, ethanol, liposome, and the like, but is not limited thereto, and may further include other typical additives such as an antioxidant and a buffer, if necessary. Further, the composition may be formulated into an injectable formulation, such as an aqueous solution, a suspension, and an emulsion, a pill, a capsule, a granule, or a tablet by additionally adding a diluent, a dispersant, a surfactant, a binder, a lubricant, and the like. With regard to suitable pharmaceutically acceptable carriers and formulations, the composition may be preferably formulated according to each ingredient by using the method disclosed in Remington's literature. The pharmaceutical composition of the present invention is not particularly limited to the dosage form, but may be formulated into an injectable agent, an inhalant, an external preparation for skin, an oral ingestible agent, or the like.

The pharmaceutical composition of the present invention may be orally administered or may be parenterally administered (for example, applied intravenously, subcutaneously, and through the skin, the nasal cavity, or the respiratory tract) according to the target method, and the administration dose may vary depending on the patient's condition and body weight, severity of disease, drug form, and administration route and period, but may be appropriately selected by the person skilled in the art.

The composition of the present invention is administered in a pharmaceutically effective amount. In the present invention, "the pharmaceutically effective amount" means an amount sufficient to treat a disease at a reasonable benefit/risk ratio applicable to medical treatment, and the level of the effective dosage can be determined according to the type and severity of disease of a patient, the activity of the drug, the sensitivity to drugs, the administration time, the administration route and release rate, the treatment duration, elements including drugs that are simultaneously used with the composition of the present invention, or other elements well-known in the medical field. The composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned elements, and this amount can be easily determined by the person skilled in the art.

Specifically, the effective amount of the composition according to the present invention may vary depending on the patient's age, sex, and body weight, and generally, 0.001 to 150 mg of the composition and preferably, 0.01 to 100 mg of the composition, per 1 kg of the body weight, may be administered daily or every other day or may be administered once to three times a day. However, since the effective amount may be increased or decreased depending on the administration route, the severity of obesity, the sex, the body weight, the age, and the like, the administration dose does not limit the scope of the present invention by any method.

As yet another aspect of the present invention, the present invention provides a method for constructing a non-viral minicircle vector to which a SOX gene is transferred, the method including the following steps:

(a) constructing a parental plasmid to which SOX genes are transferred by sequentially transferring and connecting three or two SOX genes to a parental plasmid;

(b) introducing the constructed parental plasmid into *E. coli*; and (c) obtaining a minicircle vector for expressing a SOX gene from which a bacterial backbone vector is removed by treating a culture solution of *E. coli* into which the parental plasmid is introduced with arabinose.

The three or two SOX genes in step (a) are SOX9, SOX5, and SOX6; and SOX9 and SOX6; respectively, and the genes may be sequentially transferred to a parental plasmid by using two 2A systems (E2A and T2A).

The *E. coli* in step (b) includes an *E. coli* simultaneously expressing a ΦC31 integrase and an I-SceI endonuclease, and preferably, may be *E. coli* ZYCY10P3S2T.

Hereinafter, preferred Examples for helping the understanding of the present invention will be suggested. However, the following Examples are provided only to more easily understand the present invention, and the contents of the present invention are not limited by the following Examples.

purchased from SBI, Inc., and was used as a basic backbone. The vector for constructing a minicircle is homologously recombined into two vectors of an MC site including only an exogenous gene to be expressed by arabinose induction and a bacterial backbone including antibiotic-resistant genes and a bacterial origin when proliferated in bacteria in which a ΦC31 integrase and an I-SceI endonuclease are simultaneously expressed, as illustrated in the drawing of FIG. 1. Since the vector corresponding to the bacterial backbone is naturally broken down and cleared out in the proliferation process, it is possible to obtain an MC including only an exogenous gene as a final product. Since the MC does not have a site corresponding to the bacterial backbone, there is an advantage in that a product of the produced recombinant vector can be applied directly to a clinical study. Accordingly, the present invention tried to construct polycistronic and bicistronic pMC pMC vectors in which SOX genes can be simultaneously expressed under a single promoter by using single restriction enzyme sites for gene cloning in a pMC vector.

In the SOX gene for this purpose, an MGC clone supplied by Invitrogen Corp., was purchased and used as a template for DNA PCR, and primers for PCR reactions of the respective genes are shown in the following Table 1. The genes secured after the PCR reaction were connected to the pGEM-T-Easy vector to confirm whether the gene sequence was abnormal or not through the full gene sequencing, and only the SOX gene exactly matching the gene sequence was used for cloning.

TABLE 1

| Name | Sequence (5' to 3') | SEQ ID NO: |
|---|---|---|
| SOX9-E2A-XbaI_F | TCTAGAGCCACCATGAATCTCCTGGACCCCTTCA | 3 |
| SOX9-E2A-EcoRI_R | GAATTCAGGACCGGGGTTATTACTTTCAACATCGCCAGCGAGTTTCAACAAAGCGTA GTTAGTACATTGACCCGACCCGTTTGAATGCATAGGTCGAGTGAGCTGTGT | 4 |
| SOX5-T2A-EcoRI_F | GAATTCATGTCTTCCAAGCGACCAG | 5 |
| SOX5-T2A-SwaI_R | ATTTAAATAGGGCCGGGATTCTCCTCCACGTCACCGCATGTTAGAAGACTTCCTCTG CCCTCGTTGGCTTGTCCTGCAATA | 6 |
| SOX6-SwaI_F | ATTTAAATGTCTTCCAAGCAAGCCA | 7 |
| SOX6-SalI_R | GTCGACTCAGTTGGCACTGACAGC | 8 |
| SOX9-T2A-EcoRI_R | GAATTCAGGGCCGGGATTCTCCTCCACGTCACCGCATGTTAGAAGACTTCCTCTGCC CTCAGGTCGAGTGAGCTGTGTGTA | 9 |
| SOX6-EcoRI_F | GAATTCATGTCTTCCAAGCAAGCCA | 10 |

EXAMPLES

Example 1. Construction of Non-Viral Minicircle Vector Expressing Polycistronic and Bicistronic SOX Genes 1-1. Preparation of Parental Plasmid and DNA for Transformation In order to construct a non-viral minicircle vector of the present invention, pMC.CMV-MCS-EF1-RFP(MN512A-1), which is a vector for constructing a minicircle (MC), was 1-2. Construction of Non-Viral Minicircle Vector Expressing Polycistronic and Bicistronic SOX Genes In order to construct polycistronic and bicistronic pMC vectors simultaneously expressing SOX genes, two 2A (E2A and T2A) systems were introduced such that the SOX genes could be simultaneously expressed under a single promoter (CMV) by using single restriction enzyme sites for gene cloning in a parental plasmid (pMC). The E2A and T2A sequences used in the present invention are denoted as SEQ ID NO: 11 and SEQ ID NO: 12.

More specifically, as illustrated in FIG. 2, the respective SOX genes (SOX5, SOX6, and SOX9) in which the gene base sequences prepared in Example 1-1 were confirmed were connected to the parental plasmid (pMC) in descending order of size of the gene. Accordingly, in the case of the polycistronic pMC/SOX-trio, the construction was completed by initially connecting SOX6 to the SwaI-SalI site, connecting the second largest SOX5-T2A to EcoRI-SwaI, and then finally connecting SOX9-E2A to the XbaI-EcoRI site. In the case of the bicistronic pMC/SOX-duo, the construction was completed by initially connecting SOX6 to EcoRI-SalI, and then connecting SOX9-T2A to the XbaI-EcoRI site. Both of the two completely constructed recombinant vectors were designed such that the stop codons were present only in SOX6 which is the final gene.

Example 2. Construction of Minicircle Vector (DNA)

2-1. Confirmation of Transfer of SOX Gene in Constructed SOX-Trio and SOX-Duo Vectors (pMC)

Before a minicircle vector was constructed from a parental plasmid, it was initially attempted to confirm whether SOX5, 6, or 9 genes were transferred well to the pMC/SOX-trio and pMC/SOX-duo vectors constructed by the method in Example 1. For this purpose, the vectors were treated with each restriction enzyme used during the gene cloning and allowed to react, and then electrophoresis was performed.

As a result, as illustrated in FIG. 3, when both the pMC/SOX-trio vector and the pMC/SOX-duo vector were cut by a restriction enzyme corresponding to each gene, it was confirmed by a band that an insert corresponding to the size of each gene was separated.

2-2. Construction of Minicircle Vector According to Introduction of pMC/SOX-Trio and pMC/SOX-Duo Vectors into *E. coli*

Based on the result of Example 2-1, pMC/SOX-trio and pMC/SOX-duo vectors to which SOX5, 6, and 9 genes were normally transferred were introduced into *E. coli* ZYCY10P3S2T and cultured, and then a mixture for inducing a minicircle was prepared by treating the culture medium with 0.5% arabinose. Thereafter, the vectors were additionally cultured, a DNA was extracted from the vectors, and electrophoresis was performed in order to confirm whether the minicircle DNA was properly produced.

As a result, as illustrated in FIG. 4, it was confirmed that when compared to the pMC/SOX-trio or pMC/SOX-duo vector (uncut) which was not cut by the restriction enzyme in FIG. 3, a minicircle DNA whose size was decreased by the arabinose treatment was produced.

Example 3. Verification of Chondrogenic Differentiation Efficiency by Constructed Minicircle DNA 3-1. Confirmation of Gene Expression in Adipose Stem Cells Transformed with Minicircle DNA Before verifying the chondrogenic differentiation efficiency of mesenchymal stem cells transformed with the minicircle DNA constructed according to the method in Example 2, first, it was attempted to confirm the expression levels of the SOX genes in the mesenchymal stem cells. For this purpose, the expression levels of the SOX6 and SOX9 genes transferred to the SOX-duo minicircle DNA were measured through RTPCR by transforming the SOX-duo minicircle DNA into adipose stem cells and extracting the RNA from the adipose stem cells.

As a result, as illustrated in FIG. 5, it was confirmed that due to the introduction of the minicircle DNA, SOX6 and SOX9 genes were overexpressed in adipose stem cells. In addition, as a result of performing Western blotting by extracting proteins from the adipose stem cells, as illustrated in FIG. 6, it was confirmed that SOX6 and SOX9 proteins were remarkably overexpressed at a level equal to or more than the level at which the proteins are originally expressed in cells. Through the result, it could be seen that the SOX genes could be expressed at a high level through the introduction of the minicircle DNA according to the present invention into mesenchymal stem cells.

3-2. Confirmation of Chondrogenic Differentiation Efficiency of Adipose Stem Cells Transformed with Minicircle DNA Base on the result in Example 3-1, a chondrogenic pellet differentiation inducing culture was performed for 3 weeks by using adipose stem cells transformed with the SOX-trio and SOX-duo minicircle DNAs, and then a morphological analysis of the chondrogenic pellets was performed. In this case, TGF-β and BMP7, which are growth factors during the culture, were not added to a negative control, 10 ng/ml of TGF-β and 100 ng/ml of BMP7 were added to a chondrogenic differentiation induction culture solution in a positive control, and cells were cultured for 3 weeks by replacing the culture solution with fresh culture solution every 2 or 3 days. Further, the adipose stem cells used in the negative control and the positive control were transformed with MC/RFP DNA, and growth factors TGF-β and BMP7 were not added during the chondrogenic differentiation induction of cells transformed with MC/SOX-trio and MC/SOX-duo.

As a result of observing the morphology of the chondrogenic pellet after a total of three weeks of the chondrogenic differentiation induction culture, as illustrated in FIG. 7, the chondrogenic differentiation pellets in all the groups exhibited a size slightly larger than 1 mm and did not morphologically exhibit a big difference.

Next, after RNA was extracted from the chondrogenic differentiation induction pellet and cDNA was synthesized by using the same, the expression levels of mRNAs of SOX9, Type II collagen (COLII), and aggrecan were measured through real-time PCR. As a result, as illustrated in FIG. 8, SOX9 was expressed at a higher level in cells transformed with MC/SOX-duo (SOX9-6) than in cells transformed with MC/SOX-trio (SOX-Trio) or the positive control, Type II collagen was expressed at a slightly lower level in the cells transformed with MC/SOX-duo than in the cells transformed with MC/SOX-trio, and the expression of aggrecan, which is one of the most important components of a cartilage substrate, was measured at the highest level in the cells transformed with MC/SOX-duo.

Furthermore, after a frozen tissue section was prepared by the chondrogenic differentiation induction pellet of each group, a histological analysis was performed through Safranin-O staining. As a result, as illustrated in FIG. 9, it was confirmed that the positive control and both the cell groups transformed with MC/SOX-trio (SOX-Trio) and MC/SOX-duo (SOX9-6) exhibited similar chondrogenic differentiation induction efficiencies. The results mean that even though the growth factors are not added to the culture solution during the chondrogenic differentiation induction culture, cells transformed with MC/SOX-trio and MC/SOX-duo retain a chondrogenic differentiation ability at an efficiency similar to that of the positive control.

The above-described description of the present invention is provided for illustrative purposes, and the person skilled in the art to which the present invention pertains will understand that the present invention can be easily modified into other specific forms without changing the technical spirit or essential features of the present invention. Therefore, it should be understood that the above-described Examples are only exemplary in all aspects and are not restrictive.

What is claimed is:

1. A non-viral minicircle vector comprising:
   (a) a promoter;
   (b) a gene encoding SRY (sex determining region Y)-box 6 (SOX6), and a gene encoding SRY-box 9 (SOX9); and
   (c) a gene expression cassette consisting of a terminator, wherein the non-viral minicircle vector does not comprise
   (d) a bacterial backbone;
   wherein the vector sequentially comprises the gene encoding SOX9 and the gene encoding SOX6; and
   wherein the vector consists of a base sequence of SEQ ID NO: 1 or SEQ ID NO: 2.

2. The non-viral minicircle vector of claim 1, wherein the vector consists of a base sequence of SEQ ID NO: 1.

3. The non-viral minicircle vector of claim 1, wherein the vector consists of a base sequence of SEQ ID NO: 2.

4. The non-viral minicircle vector of claim 1, wherein the promoter is a cytomegalovirus (CMV).

5. The non-viral minicircle vector of claim 1, wherein the terminator comprises an SV40 polyadenylation sequence.

6. The non-viral minicircle vector of claim 1, wherein the vector is a double-stranded DNA in a circular supercoiled form.

7. A stem cell into which the non-viral minicircle vector of claim 1 is introduced.

8. The stem cell of claim 7, wherein the stem cell is an adult stem cell.

9. A pharmaceutical composition for preventing or treating a cartilage disease, comprising the stem cell of claim 7 as an active ingredient.

10. The pharmaceutical composition of claim 9, wherein the cartilage disease is degenerative arthritis, rheumatic arthritis, ankylosing spondylitis, posttraumatic arthritis, osteochondritis dissencans, or osteomalacia.

11. The pharmaceutical composition of claim 9, wherein the composition promotes the differentiation of stem cells into chondrocytes.

12. A method for constructing a non-viral minicircle vector to which a SOX gene is transferred, the method including the following steps:
- (a) sequentially transferring and connecting (sex determining region Y)-box 9 (SOX9) and SRY-box 6 (SOX6) genes to a parental plasmid to form a constructed parental plasmid;
- (b) introducing the constructed parental plasmid into *E. coli*; and
- (c) obtaining a non-viral minicircle vector for expressing a SOX gene from which a bacterial backbone vector is removed by treating a culture solution of *E. coli* into which the parental plasmid is introduced with arabinose, wherein the non-viral minicircle vector consists of a base sequence of SEQ ID NO: 1 or SEQ ID NO: 2.

13. The method of claim 12, wherein the *E. coli* in step (b) simultaneously expresses a ΦC31 integrase and an I-SceI endonuclease.

14. The method of claim 12, wherein the non-viral minicircle vector consists of a base sequence of SEQ ID NO:1.

15. The method of claim 12, wherein the non-viral minicircle vector consists of a base sequence of SEQ ID NO: 2.

* * * * *